United States Patent [19]

Christensen et al.

[11] 4,013,924
[45] Mar. 22, 1977

[54] METHODS AND MEANS FOR DETECTING THE PRESENCE OF MOISTURE ADJACENT INSULATED PIPES

[75] Inventors: Gunnar Buhl Christensen; Ove Thastrup, both of Fredericia, Denmark

[73] Assignee: A/S E. Rasmussen, Denmark

[22] Filed: Mar. 19, 1970

[21] Appl. No.: 21,028

[52] U.S. Cl. .............................. 361/49; 174/11 R; 200/61.05; 340/235
[51] Int. Cl.[2] ......................................... H02H 7/26
[58] Field of Search ................ 174/11 R, 47, 37; 324/52; 340/235, 242; 200/61.04, 61.05; 317/10, 45

[56] References Cited

UNITED STATES PATENTS

| | | | |
|---|---|---|---|
| 1,257,452 | 2/1918 | Bowden et al. | 317/45 |
| 1,337,866 | 4/1920 | Whitaker | 317/45 |
| 2,056,085 | 9/1936 | Alles | 324/52 UX |
| 2,752,586 | 6/1956 | Jordan | 340/235 |
| 3,365,661 | 1/1968 | Zimmerman | 324/52 |
| 3,382,493 | 5/1968 | Loper et al. | 174/37 X |

FOREIGN PATENTS OR APPLICATIONS 1,122,597 1/1962 Germany .......................... 174/11

*Primary Examiner*—Harry Moose
*Attorney, Agent, or Firm*—Craig & Antonelli

[57] ABSTRACT

A method of detecting the presence of moisture adjacent the exterior side of tubes in a pipe system such as a subterranean district heating system of insulated tubes, whereby it is measured or registered whether an electrical conductivity exists between two electric conductors permanently positioned immediately adjacent the tube in supposed dry and electrical insulating but hygroscopic surroundings. Furthermore, a pipe system and a pipe having means for facilitating the use of the said method, these means comprising one or more electrical conductors extending along each pipe embedded in the insulating material surrounding the pipe.

8 Claims, 4 Drawing Figures

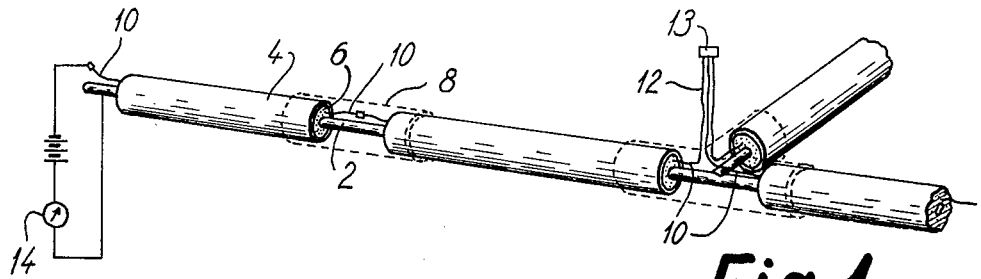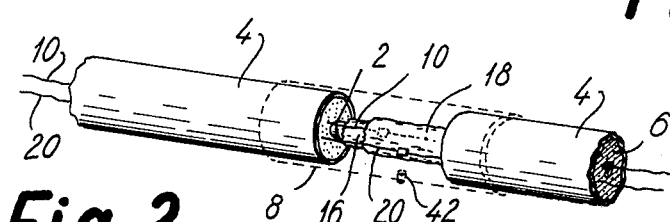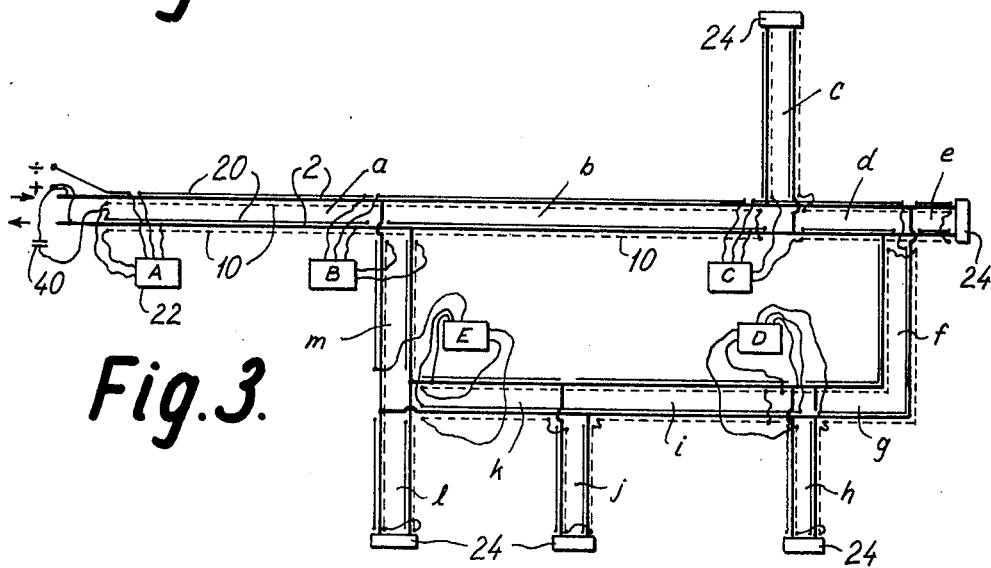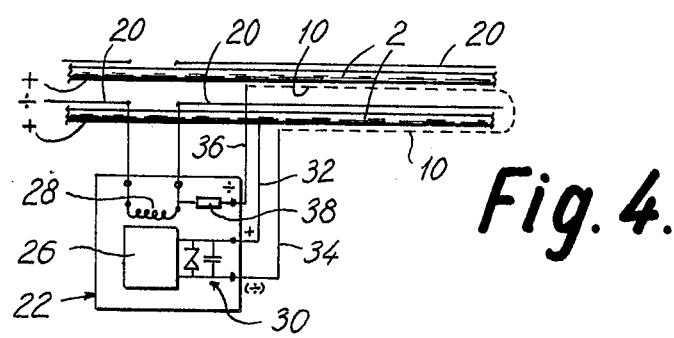

METHODS AND MEANS FOR DETECTING THE PRESENCE OF MOISTURE ADJACENT INSULATED PIPES

The present invention relates to a method for detecting the presence of moisture adjacent the exterior side of tubes in a pipe system such as a subterranean district heating system of insulated tubes. Normally, in systems of this kind, the tubes are constituted by iron tubes enclosed in a suitable insulating material, which may be molded out in situ or be provided as a prefabricated insulation around the single tube lengths. In these prefabricated pipes the insulating material, e.g. polyurethane foam is again enclosed in an outer protective tube such as a plastic tube which serves to prevent intrusion of moisture into the insulating material. At the joints between the single pipe lengths as well as at branchings from continuous pipes the conductor tubes are welded together, sufficient welding space being provided by letting the conductor tube ends project from the ends of the other parts of the pipes; when the joints have been pressure tested the exposed parts of the conductor tubes are covered in suitable manner, preferably by mounting an outer tube casing around the joints, whereby these casings will bridge the space between the adjacent ends of the exterior protective tubes, whereafter the annular space between the conductor tube and the casing is filled with a suitable insulating material through a hole in the casing.

It is extremely important that the pipe system is overall protected against intrusion of moisture into the insulating material since moisture will not only make the insulation less effective, but also over the years cause corrosion attacks on the conductor tubes. The prefabricated tubes are moisture-tight due to the said protective plastic tube, but it has been experienced that the said tube casings at the joints may cause troubles in this respect, so no matter how tight the joints are supposed to be there will still be a certain possibility that a few of them are not or will not remain absolutely tight. By a possible leakage in the system due to corrosion on the iron tube it can be extremely difficult to localise the defect because the water may run a long distance inside the plastic tubes and thereby damage the insulation and disclose itself at a point far from the leakage point.

It is the purpose of the invention to provide a method enabling a detecting or supervision of the entire system or at least particularly sensitive parts thereof in such a manner that the presence of moisture adjacent the iron tube may be registered as a warning for a possible corrosion attack on the tube.

According to the invention it is measured or registered whether an electrical conductivity exists between two electric conductors permanently positioned immediately adjacent the tube in supposed dry and electrical insulating, but hygroscopic, surroundings. If by such a measurement there is registered a conductivity above a certain threshold value, this will normally indicate that there is moisture present in the immediate surroundings of the iron tube, so that a corrosion attack can be expected. It would not be practical to use many separate measuring points in a large pipe system so preferably the measurement is carried out on the entire system from a central measuring station, whereby it is possible to realise the presence of a defect, but under circumstances not possible to localize the defect. However, there is a considerable time interval between the initial intrusion of moisture and an advanced corrosion on the iron tube, so after the defect has been registered there will be time enough to arrange a search for localizing the defect. For example this may be done by means of separate conductivity measurements on smaller sections of the system, whereby the defect may be encircled by and by. When the defect has hereby been localized to a certain part of the system it may be localized further with the use of measuring methods known for example from the localizing of short circuits in electrical cables, as described below.

The invention further comprises a pipe system provided with means for facilitating the use of the said measuring method, these means primarily comprising one or more electrical conductors mounted close to the iron tubes at least along such pipe sections which are particularly exposed to possible moisture intrusion. In a preferred embodiment the system includes a number of tone generators which as described below may be arranged so as to cause a direct indication of the approximate position of the defect in the system.

Furthermore the invention relates to a prefabricated pipe for use in the said pipe system, this pipe being provided with at least one electrical conductor embedded in the insulation and extending along the entire pipe length with its ends projecting from the ends of the pipe length. By the production of the tubes it is very easy to place these conductors in the desired position, and by the later joining of the pipes the required conductors will hereby be at disposal at the joints; also, the conductors will be placed in a perfecty protected position inside the pipes, and moreover they will enable a defect to be registered wherever the defect might occur.

In the following the invention is described in more detail with reference to the accompanying drawing in which:

FIG. 1 is a perspective view of a section of a pipe system according to the invention, FIG. 2 a corresponding view of a pipe joint, FIG. 3 a diagram of a pipe system and its associated electrical circuit, and FIG. 4 is a connection diagram for a tone generator used in the system shown in FIG. 3.

The system shown in FIG. 1 makes use of prefabricated insulated pipes, viz, pipes having an interior iron tube 2, an exterior protective mantel tube 4 of synthetic material such as polyethylene, and an insulating material 6 such as polyurethane foam filling out the annular space between the two tube members. Where the pipes are joined or branched off the conductor tubes 2 are exposed as shown so that there is space for welding the iron tubes. When the joints have been pressure tested tube casings 8 are mounted across the joints, and care is taken that the connection between the casings 8 and the plastic tubes 4 are made very tight. Preferably, after the mounting of the casing the annular space between the casing and the tube 2 is filled with an insulating material poured down through a hole in the casing so that the joints themselves are insulated.

The pipes shown are of known construction with the exception that they are provided with an electric conductor 10 extending along the iron tube through the foam material 6 which serves to hold the conductor somewhat spaced from the iron tube. At the joints the conductors 10 of the different tubes are interconnected and held in such a manner that they do not touch the iron tube. At more places in the system, preferably at branchings in inspection wells, the conductors 10 are connected through wires 12 to easily accessible measuring terminals 13. In these terminals all conductors 10, 12 are interconnected, but it is possible to disconnect any of the wires 12 therefrom.

Since the conductor system 10 is overall electrically insulated from the tubes 2 there should normally be no electrical conductivity between the system of conductors 10 and the system of tubes 2; this can be tested in simple manner from a central point by means of a measuring instrument 14 interposed between the two systems in series with a voltage source as shown in the left-hand side of FIG. 1. If by this measurement a certain conductivity between the two systems is registered, it can be counted that a moisture intrusion has taken place somewhere in the system, whereby a corrosion attack on the iron tube may start at that place. The measurement will say nothing about the location of the defect, but it is possible to encircle the defect by carrying out separate control measurements of the conductivity in restricted sections of the system, whereby the single connection wires 12 are used for this purpose, each pipe length being controlled by a measurement between the wires 12 at the ends thereof, these wires being disconnected from the terminals 13. When the defect has thus been localized to a certain pipe length it will be possible to determine the location in more detailed manner by carrying out a comparative resistance measurement between the tube 2 and the conductor 10 as measured from both ends of the pipe length, according to known measuring principles for the localising of short circuits in electrical cables.

In order to secure a correct positioning of the conductor 10 across the joints it is preferred as shown in FIG. 2 to wrap a felt layer around the exposed iron tube 2, whereafter the conductor 10 is placed along an exterior surface portion of this layer; thereafter another felt layer 18 is wrapped around the first layer so that the conductor 10 will be safely held between these two layers without being able to touch the iron tube 2. When the tube casing 8 has been mounted around the joint the remaining interior space may be filled with insulating material as described above. Especially the interior layer 16 should be of hygroscopic but dry electrical insulating material which can resist the heat from the tube 2; thus, the material does not necessarily have to be felt.

In the pipes of the system described below there is incorporated a second electrical conductor which in FIG. 2 is designated 20. This conductor is positioned along the exterior surface of the outer felt layer 18 so that it is held spaced from the conductor 10 also across the joints. In the said inspection wells both conductors 10 and 20 are led out through the casings 8 so as to be available for interconnection in the manner described below.

It will be understood that the conductivity measurement for registering a possible wet part of the insulating material may be carried out between the conductors 10 and 20 instead of between the iron tube and one of the conductors.

The detailed localization of a possible defect may be done in the most accurate manner if the conductor 10 consists of an electrically conducting resistance material such as constantan; this, however, would be disadvantageous for a central detection of the conductivity in the entire system, due to the considerable electrical resistance to the remote portions of the conductor, and it may be preferable therefore to work with both a conductor of a certain resistivity and a conductor with low resistivity, i.e., in FIG. 2 the conductor 10 may represent a constantan wire while the conductor 20 is a copper wire. The central detection and the subsequent encircling of a possible defect may then be carried out with the copper wire as the measuring conductor, while the detailed localization of the defect may be carried out by means of the constantan wire along the specific section in which the defect is present; the constantan wire is better suited to give a reliable and exact result of the said comparative resistance measurement.

The constantan wire alone might theoretically be used for both the general detection and the detailed localization of a defect if from the single junctions in the system low resistance conductors were connected to the ends of the constantan wires and drawn back to the central measuring station, i.e., if all the terminals 13 were positioned in the measuring station and connected to the terminal wires 12 by means of copper wires; the said measurements in the field for encircling and thereafter detailed localizing the defect could then be carried out from the central measuring station, but in a large pipe system it would be almost impossible to work with so many exterior connections between the terminal points and the central measuring station.

As known from the art of telecommunication it is possible, however, to substitute a great number of conductors for a single or very few conductors when the electrical signals to be transmitted through the large number of conductors are transformed to alternating currents or voltages with mutually different frequencies, whereas for the detecting of the signals there is used a corresponding number of receivers which are each tuned according to one of the actual frequencies. With the use of this principle it is possible to place electrical oscillators such as tone generators working at mutually different frequencies in different junctions in the system and in one of several possible manners let the performance of these generators be controlled by the fact whether from a measuring wire connected to the generator there is a short circuit to another conductor with another voltage, e.g., there is increased conductance between the iron tube 2 and the wire 10. The measuring wire for each single generator may control an individual limited portion of the entire pipe system, i.e., the total length of the measuring wire may be so short that the wire may well be constituted by a resistive conductor such as a constantan wire, whereby this wire is also usable for the said detailed localization of a possible defect. The other conductor 20 in the system which is of high conductivity may be used partly for the power supply to all generators and partly for constituting the said common conductor for leading the output signals from all generators to the central measuring position.

For persons skilled in the art it will be obvious that each of the tone generators may be connected to the measuring conductors such as the conductor 10 and the tube 2 in such a manner that an increased conductivity therebetween will cause a change in the frequency or intensity of the output signal from the generator. However, a frequency change might give rise to a faulty detection, and relative changes in the signal intensities would hardly constitute a good base for the measurements in a large network. According to the invention, therefore, it is preferred to let the tone generators be connected in such a manner that their power supply is short circuited in case of a short circuit between the measuring wires, whereby the output signal in case of a defect will completely disappear; this change is easy to detect in doubtless manner in the central measuring station.

The system illustrated in FIG. 3 makes use of this principle, the tone generators designated 22 being connected in the system as shown in more detail in FIG. 4. The thick full lines 2 in FIG. 3 represent the iron tubes in a part of a district heating system in which the hot water is lead in and out as indicated by arrows in the left-hand side of the figure. The single double pipe sections in the system between the different junctions and bends are designated $a$ to $m$. The sections $c$, $e$, $h$, $j$, and $l$ are connected to individual heat installations 24. In the system there is used the tubes shown in FIG. 2, and the constantan wire 10 is represented by a dotted line at one side of the tubes 2, while the copper wire 20 is represented by a full line at the other side of the tubes. In the different junctions there is established such interconnections between the wires as are clearly illustrated in FIG. 3.

Each tone generator 22 comprises an oscillator element 26, see FIG. 4, an output circuit 28, and a power supply circuit 30. The output circuit 28 is connected in series in one of the copper wires 20, this wire being connected to a negative potential relatively to a positive voltage of, e.g., 50 V supplied directly to the iron tubes 2. The positive voltage for the power supply of the generators is for each generator provided by means of a direct connection 32 to one of the tubes 2 in the junction, where the particular generator is positioned in the said inspection well. The negative voltage for the power supply is supplied by means of a connection 34 to the constantan wire 10, which extends in a loop the other end of which is connected to the negative conductor 20 through a drop resistance 38. The output circuit 28 of all generators 22 are connected in series in the copper wire 20, whereby in the sections $c$, $e$, $h$, $j$, and $l$ none of the copper wires are in use. The other end of this series connection is connected to the positive terminal of the voltage source through a condenser 40 so that the output signals from all generators are supplied to the terminals of the voltage source without any direct current ocurring in the circuit whereby the copper wire 20 will have the negative voltage overall in the system so as to be able to supply negative voltage to all generators.

The constantan wires connected to the single generators form loops along different sections of the system; as appears from FIG. 3 the generator designated A will thus serve the sections $a$ and $b$, generator B will serve the sections $m$ and $l$, the generator C will serve the sections $c$, $d$, and $e$, generator D will serve the sections $f$, $g$, and $h$, while generator E will serve the sections $i$, $j$, and K, the constantan wires along the different sections being connected in series and being electrically disconnected from the constantan wires in the other sections of the system.

As long as there is no electrical conductivity between the constantan wires 10 in the loops and the conductor tubes 2 the oscillator elements 26 will get the necessary power supply through the resistor 38 and the wires 36, 10, 34. If moisture enters the system at a certain point there will be a more or less expressed short circuit between the positive tubes 2 and the negative constantan loop which covers the particular point, whereby the supply voltage to the supply circuit 30 will be reduced until is no longer sufficient to operate the generator 26. The measuring receiver which is tuned to receive the output signal from the stopped generator will thus register the failing condition of the output signal and thereby clearly indicate the presence of a defect in the corresponding section of the pipe system. Since the particular section is automatically identified by the said receiver it is thereafter sufficient to carry out the said comparative resistance measurement directly on that section of the system which is served by the constantan loop belonging to the stopped generator.

If a certain generator shall only serve one conductor tube 2 over a given length it is of course possible to use the copper wire in this length in series with the constantan wire in order to form the measuring loop.

Instead of continuous conductors embedded in the insulating material of the pipes it will be possible to use exterior insulated wires, from which measuring wires are introduced into the insulating material 6 with suitable intervals along the particular section. The presence of water or moisture is electrically detectable also in other ways, e.g., by means of a primary electrical cell material positioned between the conductors in such a manner that between these there will be produced a measurable voltage when the material is made wet. It is also possible to use a measuring wire 10 of a material which will be rapidly corroded or dissolved by the introduction of moisture or water so as to be electrically broken, whereby the defect is detectable since the wire is no longer able to support a control current therethrough. Moreover, the portions of the wire 10 extending within the plastic tubes 4 may be substituted by a conductive coating of the interior sides of the plastic tubes.

By the mounting of the pipe system it is almost unavoidable that a certain amount of moisture is being enclosed within the tube casings 8, because the joining work is often carried out in humid surroundings. Since every effort is made to seal the tube casings moisture-tight to the exterior plastic tubes 4 this enclosed moisture will not be able to escape, and so it might give rise to a false detection of a defect. In order to rapidly obtain normal dry conditions in the system it is preferred, therefore, to mount a one-way valve 42, FIG. 2, in the wall of the each tube casing 8, these valves being adjusted so as to allow the said moisture to escape therethrough by the increased steam pressure which will occur when the hot water is sent through the tubes 2. It is not considered necessary to describe these valves in detail, since many known one-way valves will be directly usable for the purpose. For example the valves may be constructed according to the same principles as used in valves for bicycle tubes, i.e., provided with a stem having an outlet hole in the side thereof, the stem being surrounded by a piece of tube rubber, which enables an outlet from the valve but prevents introduction of air and moisture from outside to the said side hole.

Principally, the generators 22 are provided or connected with two power supply terminals or wires 32 and 34, two output terminals at 28, the two detector terminals or conductors 2 and 10. A change in the electrical conductivity between the detector conductors 2 and 10 causes a detectable change in the character of the output signal of the generator, since in the described embodiment the signal is simply stopped when a short circuit occurs between conductors 2 and 10, i.e., in this case the power supply conductors are identical with the detector conductors along the different individual sections of the system. Of course, it would alternatively be possible to suppress the output signal in response to a short circuiting between the tube 2 and the wire 10 — or between two parallel wires — under full maintenance of a separate power supply to the generator, but with the system shown the arrangement is very simple.

What we claim is:

1. A pipe system including a prefabricated conductor element for use in a subterranean fluid conductor system comprising a fluid conducting length of pipe surrounded by a dry, hygroscopic insulating foam material of artificial resin enclosed with an outer protective pipe casing of water tight material, at least one electrical wire embedded in said insulating material so as to extend along said pipe and said pipe casing in spaced relationship thereto within the insulating material, the insulating material is surrounded by a moisture tight protective tube bridged tightly by tube casings adjacent the joints between individual pipe lengths, said tube casings being provided with a one way valve in a wall portion thereof, these valves being oriented so as to allow moisture to escape from the interior of said casings.

2. A subterranean system of elongated conductor means comprising a plurality of interconnected conductor lengths each being surrounded by a layer of normally dry, hygroscopic material, and including a plurality of electrical oscillators mounted at selected places in the system, each of said oscillators having power supply terminals, signal output terminals, and detector terminals and being operable to change the character of its output signal in response to a voltage change between said detector terminals, said oscillators being adjusted so as to provide output signals of mutually different frequencies, said power supply terminals being connected to a power source through first electrical conductor means, said output terminals being connected in common to a central detecting station through second electrical conductor means, said detecting station comprising selective receiver means for the output signals from the different oscillators, said detector terminals for each oscillator being connected to respective third electrical conductor means extending along an individual section of the conduit means in said system associated with the given oscillator and at least at intervals disposed in spaced relationship in said hygroscopic material so as to be operable to change the voltage on said detector terminals in response to an increase in the electrical conductivity of said third electrical conductor means between said detector terminals.

3. A conductor system according to claim 2, in which said first electrical conductor means extend along the elongated conductor means and are connected to a common power source for said oscillations.

4. A conductor system according to claim 2, in which said second electrical conductor means extend along the elongated conductor means to said common detecting station.

5. A conductor system according to claim 2, in which said third electrical conductor means extending along each of said individual sections are identical with said first electrical conductor means for supplying power to the respective oscillator so as to be operable to stop the power supply to the oscillator in response to short circuiting of said power supply terminals by virtue of moisture being present between the power supply conductors in an area of the respective individual section of the system.

6. A prefabricated conductor element for use in a subterranean fluid conductor system comprising a fluid conducting length of pipe surrounded by a dry, hygroscopic insulating foam material of artificial resin enclosed with an outer protective pipe casing of watertight material, said insulating foam and said pipe casing having a length less than the length of said pipe to allow the respective ends thereof to extend beyond the respective ends of said insulating foam and said pipe casing, at least one electrical wire embedded in said insulating material so as to extend along said pipe and said pipe casing in spaced relationship thereto within the insulating material, the respective ends of said at least one electrical wire projecting beyond the ends of said insulating foam material and said pipe casing to facilitate interconnection with further prefabricated conductor elements in the subterranean fluid conductor system wherein said at least one wire and said pipe forming an electrical detection circuit upon connection with said at least one wire with a voltage source whereby intrusion of moisture into the conductor element can be readily detected.

7. A conductor element for use in a subterranean fluid conductor system comprising a fluid conducting length of pipe surrounded by a dry, hygroscopic insulating foam material of artificial resin enclosed with an outer protective pipe casing of watertight material, two electrical wires embedded in said insulating material so as to extend along said pipe and said pipe casing in spaced relationship thereto within said insulating material, one of said two electrical wires being a low resistance wire and the other being a wire of relatively greater electrical resistance than said low resistance wire.

8. A prefabricated conductor element for use in a subterranean fluid conductor system comprising a fluid conducting length of pipe surrounded by a dry, hygroscopic insulating foam material of artificial resin enclosed with an outer protective pipe casing of water tight material, said insulating foam and said pipe casing having a length less than the length of said pipe to allow the respective ends thereof to extend beyond the respective ends of said insulating foam and said pipe casing, at least one electrical wire embedded in said insulating material so as to extend along said pipe and said pipe casing inside said pipe casing, the respective ends of said at least one electrical wire projecting beyond the ends of said insulating foam material and said pipe casing to facilitate interconnection with further prefabricated conductor elements in the subterranean fluid conductor system, said at least one wire and at least one of said pipe and a further wire disposed inside said casing and extending in parallel, spaced relationship thereto forming an electrical detection circuit upon connection with said at least one wire with a voltage source whereby intrusion of moisture in the conductor element can be readily detected.

* * * * *